United States Patent [19]

Obermeier et al.

[11] Patent Number: 5,442,097
[45] Date of Patent: Aug. 15, 1995

[54] PROCESS FOR THE RECOVERY OF FLUORINATED CARBOXYLIC ACIDS

[75] Inventors: Reinhold Obermeier, Mühldorf; Gunter Stefaniak, Burgkirchen, both of Germany

[73] Assignee: Hoechst Aktiengesellschaft, Frankfurt am Main, Germany

[21] Appl. No.: 251,752

[22] Filed: May 31, 1994

[30] Foreign Application Priority Data

Jun. 2, 1993 [DE] Germany ............... 43 18 258.5
Jan. 29, 1994 [DE] Germany ............... 44 02 694.3

[51] Int. Cl.$^6$ ............................................. C07C 69/63
[52] U.S. Cl. ................................................. 560/227
[58] Field of Search ...................................... 560/227

[56] References Cited

U.S. PATENT DOCUMENTS

| | | |
|---|---|---|
| 4,038,231 | 7/1977 | Downer et al. |
| 4,391,940 | 7/1983 | Kuhls et al. |
| 4,639,497 | 1/1987 | Knight et al. |
| 4,730,082 | 3/1988 | Amiet ............... 560/227 |

FOREIGN PATENT DOCUMENTS

| | | | |
|---|---|---|---|
| 0206954 | 12/1986 | European Pat. Off. | ............ 560/227 |
| 0214808 | 3/1987 | European Pat. Off. | |
| 0267127 | 5/1988 | European Pat. Off. | ............ 560/227 |
| 5340708 | 4/1978 | Japan | ............ 560/227 |
| 0910599 | 3/1982 | U.S.S.R. | ............ 560/227 |

OTHER PUBLICATIONS

"Some physical properties of n-alkyl trifluoroacetates" Jeffery et al; J. Appl. Chem., 10, Jan., 1960.
Patent Abstracts of Japan, vol. 14, No. 137, p. 702 (Mar. 15, 1990).

*Primary Examiner*—Joseph L. Schofer
*Assistant Examiner*—N. Sarofim
*Attorney, Agent, or Firm*—Connolly and Hutz

[57] ABSTRACT

Fluorinated carboxylic acids can be recovered from materials which contain them by releasing, if necessary, the carboxylic acids with sufficiently strong acids, esterifying the released acids and distilling off the esters. The esters can be advantageously directly hydrolyzed with aqueous ammonia solution to give the corresponding ammonium salts.

9 Claims, No Drawings

PROCESS FOR THE RECOVERY OF FLUORINATED CARBOXYLIC ACIDS

For the polymerization of fluorinated monomers in aqueous dispersion, fluorinated emulsifiers are used since these do not exhibit telogenic activity. Readily soluble salts of perfluorocarboxylic acids are principally used, in particular the ammonium salt of perfluorooctanoic acid. For this purpose, the underlying acids must have a high purity, since impurities can inhibit or even prevent the initiation of polymerization, interferences in the course of polymerization, for example as a result of chain transfer, can occur or polymerization can be terminated.

These purity criteria have hitherto made the recovery of the said acids very difficult and extremely complex. A complicating factor in this case is that the acids, during the recovery by scrubbing with alkalis, for example from the exhaust air, display their surfactant action by forming a foam which is difficult to deal with. Defoamers are therefore frequently used, which further complicate work-up of the underlying acids.

If attempts are made to release the acids from such mixtures—for example using sulfuric acid—and then to isolate them by distillation, they fail since these acids form crystallizing hydrates which can block up the distillation equipment. Moreover, distillation residues are produced in this case which still contain considerable amounts of fluorine and the disposal of which is very complex.

A process has now been found which permits the utilization of the said fluorinated carboxylic acids from mixtures in which these acids can also be present as salts, which process does not have the said disadvantages. According to the invention, for this purpose the fluorinated carboxylic acid is, if necessary, released from the starting material in an aqueous medium with a sufficiently strong acid and reacted with a suitable alcohol to form an ester which is separated off by distillation. If release of the carboxylic acid from its salt is not required, a catalytic amount of acid is sufficient for the esterification.

Suitable starting materials are solid and liquid products which contain salts of the fluorinated carboxylic acids. In practice in this case these are the ammonium salts or sodium salts, but analogous salts such as potassium salts are not excluded. The starting materials, apart from the abovementioned defoamers, can also further contain other inorganic or organic impurities if these do not form volatile compounds which interfere in the distillation of the desired ester.

The starting material used can advantageously be a polymerization liquor. The preferred starting material is a liquor from the emulsion polymerization of fluorinated polymers. These can be used directly after separating off the polymer, that is without concentration. Emulsion polymerization is described, for example, in U.S. Pat. No. 4,391,940 (and the earlier literature cited therein).

The sufficiently strong acid used in practice to release the fluorinated carboxylic acid is sulfuric acid. However, other acids having equivalent action are not intended to be excluded.

The alcohol component which is primarily useful is methanol, since it is inexpensive and forms a readily volatile ester. The use of other alcohols, for example ethanol or isopropanol, is possible but does not provide any advantages.

Further advantageous embodiments of the invention are described in more detail below, only the preferred reaction participants or reagents being mentioned in each case for the sake of simplicity. Perfluorooctanoic acid is abbreviated in this case to "PFOA". Percentages are by weight unless otherwise stated.

A distillation vessel is charged with aqueous sulfuric acid, preferably 60% strength sulfuric acid, in an amount such that PFOA is released from the starting material subsequently introduced, for example from the sodium salt of PFOA—in solution, in solid form or as a suspension which can still contain free sodium hydroxide solution. The said suspension expediently contains about 1 to about 70%, advantageously about 5 to about 40%, of the sodium salt and no more than 40% of free sodium hydroxide solution. When a polymerization liquor is used, the content of PFOA salt is considerably lower, for example 0.01 to 0.1%. An excess amount of methanol, expediently 10 mol per mole of PFOA is then added, and the reaction mixture is slowly heated to a bottom temperature of about 70° to about 90° C., preferably 85° C. From this temperature, a ternary mixture of water, methanol and PFOA methyl ester distills over, which mixture separates into two phases after condensation. The bottom, denser phase (density 1.7 g/cm$^3$) comprises more than 98% of PFOA methyl ester and the top phase comprises a mixture of methanol and water. The bottom phase is separated off and the top phase is returned to the process. The distillation is continued until no phase separation occurs any longer in the distillate. The remaining methanol/water mixture is separated off, expediently distilled off, and reused for a following batch. The distillation residue remaining is an aqueous solution containing about 25% of sodium sulfate and about 5% of sulfuric acid and containing only about 0.1% of organic matter and only about 0.01% of fluorine.

In the preferred embodiment of the invention using a crude polymerization liquor, to this is added a small amount, for example 2 to 5%, of alcohol, preferably methanol, the liquor is made sufficiently acidic with a strong acid, preferably sulfuric acid, preferably to a pH of about 1 to 2, and the ester formed is distilled off. If the crude polymerization liquor still contains small amounts of finely divided polymer, the turbid liquor clears in this case, the polymer arising in an easily separable form. The treatment according to the invention therefore separates off the surface-active fluorinated carboxylic acid to a very high degree. This is also shown by the original fluorine content of the liquor being considerably reduced.

In a particularly preferred embodiment of the invention, the PFOA methyl ester is directly converted into the ammonium salt of PFOA. Surprisingly, the crude ester arising can be directly hydrolyzed for this with aqueous ammonia solution, as a result of which a product is isolated in the required purity.

Advantageously, aqueous ammonia solution of an ammonia content of expediently 25% and water are introduced for this into an agitator vessel and the crude ester is added to this. The mixture is heated to about 70° to 95° C. and stirred until the initially turbid reaction mixture becomes completely clear. At a bottom temperature of about 95° C., a mixture of methanol and water is then distilled off which can be used for the esterification. The remaining solution of the ammonium salt of PFOA can—if necessary after filtration—be used directly as an emulsifier for the polymerization of fluorinated monomers. The amide content is less than 0.1%.

In particular in the abovementioned preferred embodiment the expensive valuable material PFOA ammonium salt has therefore been successfully recovered in an elegant, simple process in high yield and the required purity from heavily contaminated starting materials. It is particularly advantageous that in this process no wastes are obtained which are difficult to dispose of, even if the material used contains impurities such as defoamers.

The PFOA methyl ester produced can obviously be further processed in other ways, for example hydrolyzed to give free PFOA. Since an ester represents an activated acid derivative, other conventional further processing measures are clearly also possible, such as transesterifications or conversion into amides.

The invention is described in more detail in the following examples. Unless otherwise stated, percentages and parts are by weight.

EXAMPLE 1

2000 parts of 60% strength sulfuric acid are introduced into an agitator vessel and heated to 50° C. 3000 parts of PFOA sodium salt are then added with stirring in the form of a suspension which contains 15% of the sodium salt and 25% of sodium hydroxide. In this case, the temperature is kept at about 60° C. by cooling. 350 parts of methanol are then slowly added and the mixture is gradually heated. From a bottom temperature of 85° C., a ternary mixture of water, methanol and PFOA methyl ester distills over. The distillate separates after condensation into two phases: the bottom phase (density 1.7 g/cm$^3$) comprises PFOA methyl ester having a purity greater than 98%, the top phase comprises 70% strength methanol. The top phase is returned to the distillation vessel and the process is continued until no phase separation can be observed any longer in the condensate.

The excess methanol is distilled off as 70% strength methanol/water mixture and used for a following batch. The distillation residue comprises water having a total fluorine content of 0.01%, a sodium sulfate content of about 25%, a sulfuric acid content of about 5% and a content of organic matter of about 0.1%, equivalent to a COD value of 1500 mg of O$_2$/kg.

EXAMPLE 2

A crude liquor from the copolymerization of tetrafluoroethylene and perfluoro-(n-propyl vinyl) ether, in which the ammonium salt of PFOA was used as emulsifier, serves as starting material. The total fluorine content of the liquor is 0.14%.

4000 g of this liquor together with 120 g of methanol are placed in an agitator vessel and then 60% strength sulfuric acid is added so that a pH of 1 is established. The mixture is heated to boiling so that a mixture of methanol, PFOA methyl ester and water slowly distills off. The initially turbid liquor becomes completely clear in this case, a white precipitate of the polymer forming.

The distillate separates after condensation into two phases: the bottom phase (density 1.7 g/cm$^3$) comprises PFOA methyl ester, the top phase comprises 70% strength methanol. This is separated off and is used in a following batch. The process is continued until no phase separation can be observed any longer in the condensate. The clear filtrate of the distillation residue contains about 10 ppm of fluorine.

EXAMPLE 3

Example 2 is repeated with a crude liquor which originates from the homopolymerization of tetrafluoroethylene by the emulsion process with the ammonium salt of PFOA as emulsifier. The crude liquor has a total fluorine content of 0.02%, after the treatment of about 10 ppm.

EXAMPLE 4

1504 parts of water and 150 parts of 25% strength ammonia solution are placed in a distillation vessel and 428 parts of PFOA methyl ester are slowly added with stirring. The mixture is initially heated to 75° C., stirred at this temperature for 30 minutes and then stirred for 5 hours at 90° C. The initially turbid mixture becomes completely clear in this case. The mixture is further heated up to about 95° C. bottom temperature, 680 parts of a roughly 5% strength methanol/water mixture distilling over at a top temperature of 70° to 99° C. The distillation residue remaining is an aqueous solution having a content of 30% of PFOA ammonium salt which—if necessary after filtration—can be used directly as emulsifier for the polymerization of fluorinated monomers.

We claim:

1. A process for the recovery of fluorinated carboxylic acid emulsifiers in utilizable form from contaminated starting materials, which comprises:
   optionally releasing the fluorinated carboxylic acid from these materials in an aqueous medium with a sufficiently strong acid,
   reacting this fluorinated carboxylic acid with a suitable alcohol and
   distilling off the ester thus formed.

2. The process as claimed in claim 1, wherein the starting material contains perfluorooctanoic acid or a salt thereof.

3. The process as claimed in claim 1, wherein the starting material contains the fluorinated carboxylic acid as ammonium salt or sodium salt.

4. The process as claimed in claim 1, wherein the starting material is a liquor from the emulsion polymerization of fluorinated polymers.

5. The process as claimed in claim 1, wherein the alcohol is methanol.

6. The process as claimed in claim 1, wherein the sufficiently strong acid is sulfuric acid.

7. A process for the recovery of a fluorinated carboxylic acid emulsifier from an aqueous medium containing a salt of said fluorinated carboxylic acid emulsifier, which comprises:
   converting said salt of a fluorinated carboxylic acid to the corresponding carboxylic acid while said salt is in said aqueous medium, thereby obtaining a fluorinated carboxylic acid in said aqueous medium,
   reacting this fluorinated carboxylic acid with an alcohol which will react with said fluorinated carboxylic acid to form a volatilizable fluorinated carboxylic acid ester, thereby obtaining a volatilizable fluorinated carboxylic acid ester, and
   distilling off and recovering said volatilizable fluorinated carboxylic acid ester.

8. The process as claimed in claim 7, wherein said alcohol is a $C_1$-$C_3$ alcohol.

9. The process as claimed in claim 7, wherein the starting material contains perfluorooctanoic acid or a salt thereof.

* * * * *